US008702727B1

(12) United States Patent
Harrington et al.

(10) Patent No.: US 8,702,727 B1
(45) Date of Patent: Apr. 22, 2014

(54) DELIVERY CATHETER WITH IMPLANT EJECTION MECHANISM

(75) Inventors: Douglas C. Harrington, San Jose, CA (US); Daniel P. Rogy, San Jose, CA (US); Victor E. Viray, Sunnyvale, CA (US)

(73) Assignee: Hologic, Inc., Bedford, MA (US)

( * ) Notice: Subject to any disclaimer, the term of this patent is extended or adjusted under 35 U.S.C. 154(b) by 1080 days.

(21) Appl. No.: 11/562,882

(22) Filed: Nov. 22, 2006

Related U.S. Application Data

(63) Continuation-in-part of application No. 10/812,476, filed on Mar. 29, 2004, now Pat. No. 7,842,035, which is a continuation of application No. 09/810,761, filed on Mar. 16, 2001, now Pat. No. 6,712,810, which is a continuation of application No. 09/241,790, filed on Feb. 1, 1999, now Pat. No. 6,309,384.

(51) Int. Cl.
*A61D 1/06* (2006.01)
*A61F 11/00* (2006.01)

(52) U.S. Cl.
USPC .......................................... 606/135; 606/108

(58) Field of Classification Search
USPC .......... 606/135, 140, 108; 128/842, 843, 824; 604/57, 60–64, 68, 134, 135, 140, 141, 604/143
See application file for complete search history.

(56) References Cited

U.S. PATENT DOCUMENTS

| 2,102,270 | A |   | 12/1937 | Hyams |
|---|---|---|---|---|
| 3,175,646 | A | * | 3/1965 | Wilcox ........................ 188/297 |
| 3,680,542 | A |   | 8/1972 | Cimber |
| 3,805,767 | A |   | 4/1974 | Erb |
| 3,840,016 | A |   | 10/1974 | Lindemann |
| 3,858,571 | A |   | 1/1975 | Rudolph |
| 3,858,586 | A |   | 1/1975 | Lessen |
| 3,918,431 | A |   | 11/1975 | Sinnreich |
| 3,938,527 | A |   | 2/1976 | Rioux et al. |
| 3,949,736 | A |   | 4/1976 | Vrana et al. |
| 3,953,566 | A |   | 4/1976 | Gore |
| RE29,345 | E |   | 8/1977 | Erb |
| 4,052,754 | A |   | 10/1977 | Homsy |
| 4,057,063 | A |   | 11/1977 | Gieles et al. |
| 4,185,618 | A |   | 1/1980 | Corey |
| 4,245,643 | A |   | 1/1981 | Benzing, III et al. |
| 4,258,721 | A |   | 3/1981 | Parent et al. |

(Continued)

FOREIGN PATENT DOCUMENTS

| AU | B-59403/96 | 2/1997 |
|---|---|---|
| CA | 2182738 | 10/2000 |

(Continued)

OTHER PUBLICATIONS

Dictionary.com; definitition of coupled; retrieved Sep. 30, 2011 from http://dictionary.com/browse/coupled.*

(Continued)

*Primary Examiner* — Tuan V Nguyen
*Assistant Examiner* — Tin Nguyen
(74) *Attorney, Agent, or Firm* — Vista IP Law Group LLP

(57) ABSTRACT

A delivery catheter with a plug ejection mechanism with a fluid filled actuator incorporated in the catheter's handle is disclosed. After delivery of RF energy, the clinician deploys the plug within the region of the lesion by activating the plug ejection mechanism.

6 Claims, 5 Drawing Sheets

(56) References Cited

U.S. PATENT DOCUMENTS

| | | |
|---|---|---|
| 4,311,145 A | 1/1982 | Esty et al. |
| 4,345,602 A | 8/1982 | Yoshimura et al. |
| 4,416,660 A | 11/1983 | Dafoe |
| 4,474,179 A | 10/1984 | Koch |
| 4,509,504 A | 4/1985 | Brundin |
| 4,512,342 A | 4/1985 | Zaneveld |
| 4,523,590 A | 6/1985 | Roth et al. |
| 4,537,186 A | 8/1985 | Verschoof et al. |
| 4,606,336 A | 8/1986 | Zeluff |
| 4,641,634 A | 2/1987 | Storz |
| 4,700,701 A | 10/1987 | Montaldi |
| 4,779,611 A | 10/1988 | Grooters et al. |
| 4,788,966 A | 12/1988 | Yoon |
| 4,793,326 A | 12/1988 | Shishido |
| 4,834,091 A | 5/1989 | Ott |
| 4,907,158 A | 3/1990 | Kettler et al. |
| 4,966,597 A | 10/1990 | Cosman |
| 4,994,069 A | 2/1991 | Ritchart et al. |
| 5,009,655 A | 4/1991 | Daignault, Jr. et al. |
| 5,095,917 A | 3/1992 | Vancaillie |
| 5,122,137 A | 6/1992 | Lennox |
| 5,147,353 A | 9/1992 | Everett |
| 5,152,784 A | 10/1992 | Tsilibary |
| 5,167,658 A | 12/1992 | Ensslin |
| 5,203,344 A | 4/1993 | Scheltinga et al. |
| 5,303,719 A | 4/1994 | Wilk et al. |
| 5,304,194 A | 4/1994 | Chee et al. |
| 5,320,091 A | 6/1994 | Grossi et al. |
| 5,341,807 A | 8/1994 | Nardella |
| 5,366,476 A | 11/1994 | Noda |
| 5,383,922 A | 1/1995 | Zipes et al. |
| 5,391,146 A | 2/1995 | That et al. |
| 5,395,342 A | 3/1995 | Yoon |
| 5,458,585 A | 10/1995 | Salmon et al. |
| 5,458,640 A | 10/1995 | Gerrone |
| 5,460,628 A | 10/1995 | Neuwirth et al. |
| 5,469,857 A | 11/1995 | Laurent et al. |
| 5,490,845 A | 2/1996 | Racz |
| 5,505,686 A | 4/1996 | Willis et al. |
| 5,531,741 A | 7/1996 | Barbacci |
| 5,536,267 A | 7/1996 | Edwards et al. |
| RE35,330 E | 9/1996 | Malone et al. |
| 5,556,396 A | 9/1996 | Cohen et al. |
| 5,569,242 A | 10/1996 | Lax et al. |
| 5,569,245 A | 10/1996 | Guglielmi et al. |
| 5,569,462 A | 10/1996 | Martinson et al. |
| 5,581,487 A | 12/1996 | Kelly et al. |
| 5,589,176 A | 12/1996 | Seare, Jr. |
| 5,601,600 A | 2/1997 | Ton |
| 5,605,693 A | 2/1997 | Seare, Jr. |
| 5,617,319 A | 4/1997 | Arakawa et al. |
| 5,632,767 A | 5/1997 | Sinofsky |
| 5,635,482 A | 6/1997 | Bhatnagar |
| 5,643,253 A | 7/1997 | Baxter et al. |
| 5,643,257 A | 7/1997 | Cohen et al. |
| 5,649,924 A | 7/1997 | Everett et al. |
| 5,658,282 A | 8/1997 | Daw et al. |
| 5,673,704 A | 10/1997 | Marchlinski et al. |
| 5,743,905 A | 4/1998 | Eder et al. |
| 5,746,769 A | 5/1998 | Ton et al. |
| 5,785,705 A | 7/1998 | Baker |
| 5,785,706 A | 7/1998 | Bednarek |
| 5,800,529 A | 9/1998 | Brauker et al. |
| 5,810,810 A | 9/1998 | Tay et al. |
| 5,827,269 A | 10/1998 | Saadat |
| 5,830,222 A | 11/1998 | Makower |
| 5,836,875 A | 11/1998 | Webster, Jr. |
| 5,836,990 A | 11/1998 | Li |
| 5,891,457 A | 4/1999 | Neuwirth |
| 5,935,137 A | 8/1999 | Saadat et al. |
| 5,954,715 A | 9/1999 | Harrington et al. |
| 5,979,446 A | 11/1999 | Loy |
| 6,042,590 A | 3/2000 | Sporri et al. |
| 6,059,779 A | 5/2000 | Mills |
| 6,066,139 A | 5/2000 | Ryan et al. |
| 6,068,626 A | 5/2000 | Harrington et al. |
| 6,071,283 A | 6/2000 | Nardella et al. |
| 6,080,152 A | 6/2000 | Nardella et al. |
| 6,091,995 A | 7/2000 | Ingle et al. |
| 6,096,052 A | 8/2000 | Callister et al. |
| 6,145,505 A | 11/2000 | Nikolchev et al. |
| 6,176,240 B1 | 1/2001 | Nikolchev et al. |
| 6,264,653 B1 | 7/2001 | Falwell |
| 6,309,384 B1 | 10/2001 | Harrington et al. |
| 6,346,102 B1 | 2/2002 | Harrington et al. |
| 6,391,024 B1 | 5/2002 | Sun et al. |
| 6,401,719 B1 | 6/2002 | Farley et al. |
| 6,432,116 B1 | 8/2002 | Callister et al. |
| 6,526,979 B1 | 3/2003 | Nikolchev et al. |
| 6,565,557 B1 | 5/2003 | Sporri et al. |
| 6,569,160 B1 | 5/2003 | Goldin et al. |
| 6,595,989 B1 | 7/2003 | Schaer |
| 6,634,361 B1 | 10/2003 | Nikolchev et al. |
| 6,637,962 B1 | 10/2003 | Roche et al. |
| 6,679,266 B2 | 1/2004 | Nikolchev et al. |
| 6,682,477 B2 | 1/2004 | Boebel et al. |
| 6,684,884 B2 | 2/2004 | Nikolchev et al. |
| 6,705,323 B1 | 3/2004 | Nikolchev et al. |
| 6,709,667 B1 | 3/2004 | Lowe et al. |
| 6,712,810 B2 | 3/2004 | Harrington et al. |
| 6,726,682 B2 | 4/2004 | Harrington et al. |
| 6,763,833 B1 | 7/2004 | Khera et al. |
| 6,780,182 B2 | 8/2004 | Bowman et al. |
| 6,871,085 B2 | 3/2005 | Sommer |
| 6,871,650 B1 | 3/2005 | Nikolchev et al. |
| 6,964,274 B1 | 11/2005 | Ryan et al. |
| 6,972,018 B2 * | 12/2005 | Ryan et al. ............. 606/50 |
| 7,073,504 B2 | 7/2006 | Callister et al. |
| 7,195,630 B2 | 3/2007 | Ciarrocca |
| 7,220,259 B2 | 5/2007 | Harrington et al. |
| 7,237,552 B2 | 7/2007 | Khera et al. |
| 7,398,780 B2 | 7/2008 | Callister et al. |
| 7,428,904 B2 | 9/2008 | Nikolchev et al. |
| 7,506,650 B2 | 3/2009 | Lowe et al. |
| 7,582,085 B2 | 9/2009 | Bowman et al. |
| 7,635,382 B2 | 12/2009 | Pryor |
| 2002/0177855 A1 | 11/2002 | Greene et al. |
| 2002/0188195 A1 | 12/2002 | Mills |
| 2003/0032936 A1 | 2/2003 | Lederman |
| 2004/0186423 A1 | 9/2004 | Cafferata |
| 2004/0255958 A1 * | 12/2004 | Harrington et al. ........... 128/898 |
| 2004/0267308 A1 * | 12/2004 | Bagaoisan et al. ............ 606/213 |
| 2005/0033402 A1 * | 2/2005 | Cully et al. ................ 623/1.11 |
| 2005/0045183 A1 | 3/2005 | Khera et al. |
| 2005/0143817 A1 | 6/2005 | Hunter et al. |
| 2006/0116635 A1 | 6/2006 | Van Heugten |
| 2007/0135830 A1 | 6/2007 | Schaeffer |
| 2007/0173883 A1 | 7/2007 | Keegan et al. |
| 2007/0196158 A1 | 8/2007 | Roche et al. |
| 2008/0135053 A1 | 6/2008 | Gruber et al. |
| 2009/0056722 A1 | 3/2009 | Swann |
| 2009/0281558 A1 | 11/2009 | Li |
| 2011/0180073 A1 | 7/2011 | Callaghan et al. |
| 2011/0202077 A1 * | 8/2011 | Chin et al. .................... 606/153 |

FOREIGN PATENT DOCUMENTS

| | | |
|---|---|---|
| DE | 3917179 | 12/1989 |
| EP | 0 105 669 | 4/1984 |
| EP | 0 153 190 | 8/1985 |
| EP | 0 541 258 | 5/1993 |
| EP | 0 752 236 | 1/1997 |
| EP | 1 554 999 | 7/2005 |
| GB | 2 359 492 | 8/2001 |
| WO | WO96/40023 | 12/1996 |
| WO | WO96/40024 | 12/1996 |
| WO | WO97/17030 | 5/1997 |
| WO | WO97/49345 | 12/1997 |
| WO | WO98/55046 | 12/1998 |

(56) References Cited

FOREIGN PATENT DOCUMENTS

| | | |
|---|---|---|
| WO | WO01/91834 | 12/2001 |
| WO | WO02/28311 | 4/2002 |

OTHER PUBLICATIONS

Brumsted, Attempted Transcervical Occlusion of the Fallopian Tube with the ND: Yag Laser, 77 Obstetrics and Gynecology 327-28 (Feb. 1991).

Coleman, The Foreign Body Reaction: A Chronic Inflammatory Response, 8 J. Biomed. Mater. Res. 199-211 (1974).

Conceptus Incorporated, Summary of Safety and Effectiveness Data, P020014, Nov. 4, 2002.

Kearney, Patent Cooperation Treaty Written Opinion, International Application No. PCT/US98/08111, Date of Mailing Feb. 22, 1999.

Neuwirth, Update on Transcervical Sterilization, 51 International Journal of Gynecology & Obstetrics, Suppl, 1, S23-28 (1995).

Phillips, Experimental Closure of Arteriovenous Fistula by Transcatheter Electrocoagulation, 115 Radiology 319-21 (May 1975).

Pollack, Wound Healing: A Review, 5:5 J. Dermatol. Surg. Oncol. 389 (May 1979).

Quinones Guerror, Tubal Electrocauterization Under Hysteroscopic Control, 7 Contraception 195-201 (Mar. 1973).

Quinones, Hysteroscopic Sterilization, 14 International Journal of Gynecology & Obstetrics 27-34 (1976).

Sahwi, The Leukocytic Response to an Intrauterine Foreign Body in the Rabbit, 22 Fertility and Sterility 398 (Jun. 1971).

Thompson, Vessel Occlusion with Transcatheter Electrocoagulation: Initial Clinical Experience, 133 Radiology 335-340 (Nov. 1979).

Tibbs, Wound Healing Following Radiation Therapy: A Review, 42 Radiology and Oncology 99-106 (1977).

Office Action mailed Oct. 10, 2006, U.S. Appl. No. 10/812,476, filed Mar. 29, 2004 In Re: Douglas C. Harrington, "Method & Apparatus for Tubal Occlusion".

Office Action mailed Nov. 14, 2006, U.S. Appl. No. 10/924,584, filed Aug. 24, 2004 In Re: Brett S. Bowman, "Catheter Placement Detection System & Operator Interface".

Office Action mailed Feb. 21, 2008, U.S. Appl. No. 10/812,476, filed Mar. 29, 2004 In Re: Douglas C. Harrington, "Method & Apparatus for Tubal Occlusion".

Office Action mailed Feb. 7, 2008, U.S. Appl. No. 10/924,584, filed Aug. 24, 2004 In Re: Brett S. Bowman, "Catheter Placement Detection System & Operator Interface".

Office Action mailed Jul. 31, 2007, U.S. Appl. No. 10/924,584, filed Aug. 24, 2004 In Re: Brett S. Bowman, "Catheter Placement Detection System & Operator Interface".

Dictionary.com; definition of coupled; retrieved Sep. 30, 2011 from http://dictionary.com/browse/coupled.

\* cited by examiner

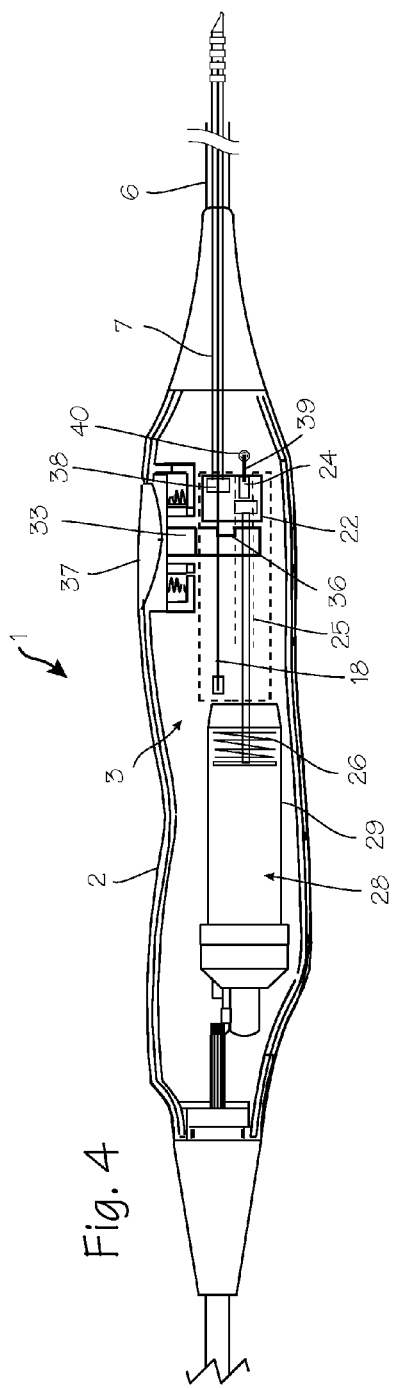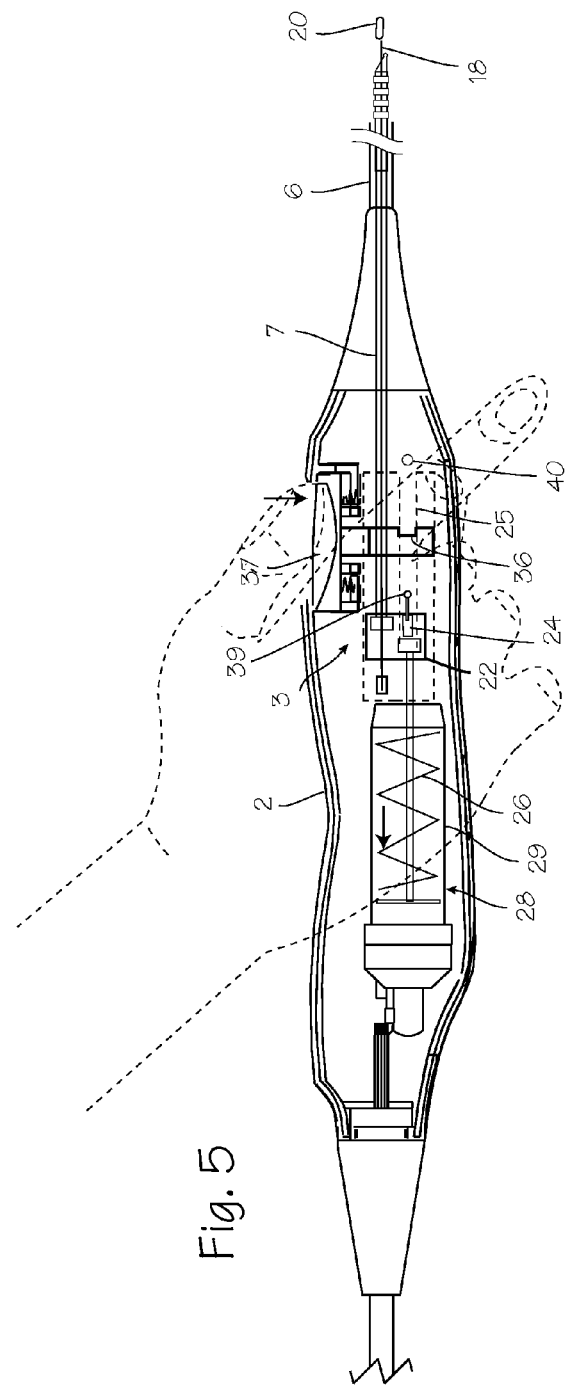
Fig. 4
Fig. 5

US 8,702,727 B1

DELIVERY CATHETER WITH IMPLANT EJECTION MECHANISM

CROSS-REFERENCE TO RELATED APPLICATIONS

The present application is a continuation-in-part of application Ser. No. 10/812,476, filed Mar. 29, 2004, now U.S. Pat. No. 7,842,035, which is a continuation of application Ser. No. 09/810,761, filed Mar. 16, 2001, now U.S. Pat. No. 6,712,810, which is a continuation of application Ser. No. 09/241,790, filed on Feb. 1, 1999, now U.S. Pat. No. 6,309,384.

FIELD OF THE INVENTIONS

The inventions described below relates to a system and method for implanting devices in the fallopian tubes or other vessels of the body.

BACKGROUND OF THE INVENTIONS

In our prior U.S. patent, Harrington, et al., Flexible Method and Apparatus for Tubal Occlusion, U.S. Pat. No. 6,309,384 (Oct. 30, 2001), we described devices and methods for sterilization of female patients. Our sterilization method involves thermally wounding a small area of the patient's utero-tubal junction with relatively low power, and placing a foam plug within the wounded area. The method is facilitated by our catheter system, which comprises a catheter with a wounding segment which fits into the utero-tubal junction and carries the plug. The wounding segment comprises a short tubular extension slidably mounted within the distal tip of the catheter. The foam plug is stored within the wounding segment. The plug is deposited in the ovarian pathway when the wounding segment is retracted over the plug (a stationary holding rod within the catheter holds the plug in place relative to the catheter, so that retraction of the wounding segment exposes the plug).

SUMMARY

The systems and methods described below provide for smooth ejection or release of a contraceptive plug or other implant in a system requiring retraction of a sheath to eject or release the implant. A plug ejection mechanism is incorporated into the catheter system to retract the sheath within a catheter body while holding the plug in place, thereby exposing the plug. The plug ejection mechanism comprises the sheath, a push rod inside the sheath, and a sheath retraction mechanism which includes a dashpot with a fluid filled chamber and a piston, a pre-loaded spring operably fixed to the sheath, and a latch that prevents any motion of the components until the mechanism is unlatched by the user. A push-button or solenoid-operated unlatching mechanism is provided to release the latch, thereby releasing the spring in the dashpot, thereby drawing the catheter sheath proximally. The fluid-filled chamber of the dashpot dampens the spring action to provide smooth and whip-less ejection of the plug from the sheath.

BRIEF DESCRIPTION OF THE DRAWINGS

FIG. 4 illustrates the delivery catheter with the plug ejection mechanism as it is configured prior to ejection of the plug.
FIG. 5 illustrates the delivery catheter as it is configured after the plug ejection mechanism has been activated and the plug has been uncovered.

DETAILED DESCRIPTION OF THE INVENTIONS

Figure 1:
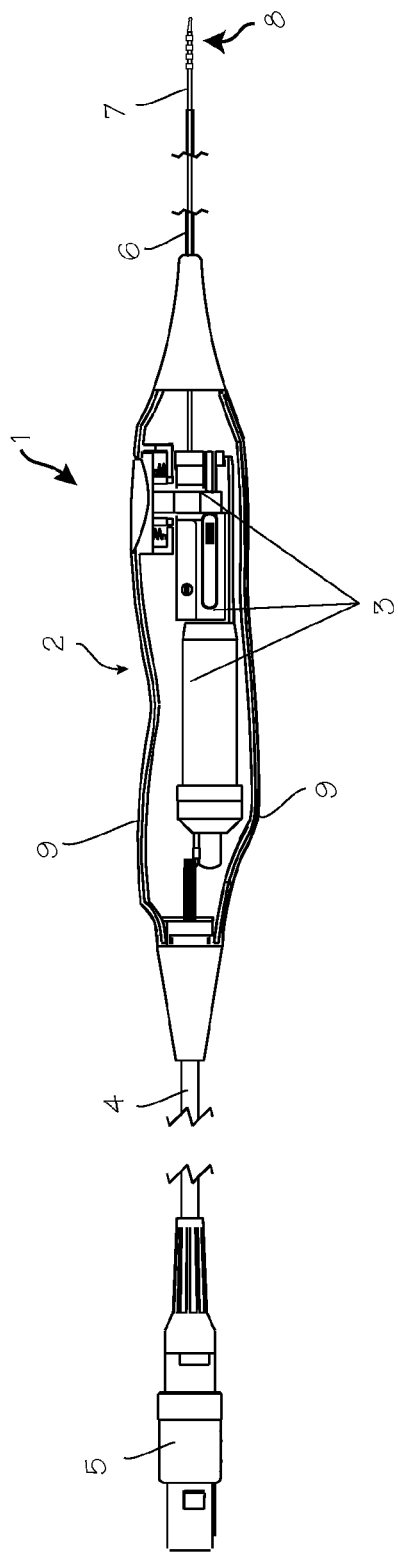
FIG. 1 shows a sectional view of the delivery catheter illustrating the main components of the delivery catheter.

FIG. 1 is a sectional view of the delivery catheter 1 illustrating the main components of delivery catheter 1. The delivery catheter 1 comprises an ergonomic handle 2 housing a sheath retraction mechanism 3, a cable 4 with an electrical connector 5, a catheter body or shaft 6, a sheath 7 and a plug (not visible in the view) disposed within the wounding segment 8. The sheath 7 comprises a tube slidably disposed within the catheter body 6. The sheath extends proximally to the handle and distally from the distal end of the catheter body 6. The handle comprises a housing 9 which contains the sheath retraction mechanism 3 and support structures for the catheter body, connectors and other components, and provides an ergonomic handgrip for the clinician. The cable and connector are suitable for connection to a power source and control system, which is operable to provide power to the wounding segment.

Figure 2:
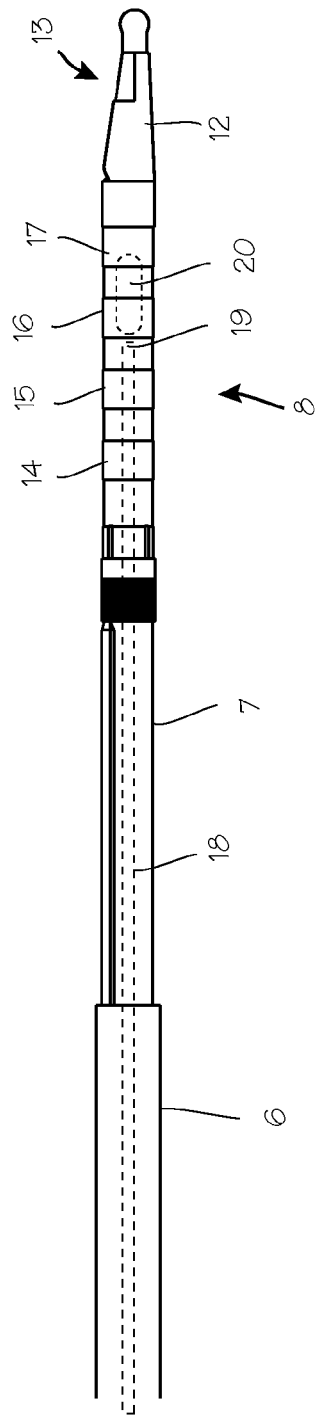
FIG. 2 shows the distal portion of the delivery catheter.

FIG. 2 shows the distal portion of the delivery catheter, including the distal portion of the sheath which protrudes distally from the distal end of the catheter body 6. The distal portion of the sheath 7 comprises the wounding segment 8 coupled to a tapered atraumatic distal tip 12. A plug exit slit 13 is located on one side of the sheath approximately 3 mm proximal to the end of the distal tip. Electrodes 14, 15, 16 and 17 on the outer surface of the wounding segment 8 are operable to lightly wound the ovarian pathway as described in Harrington, U.S. Pat. No. 6,309,384. A push rod assembly 18 is disposed within the sheath and catheter body. The distal tip 19 of the push rod is located within the internal diameter of the sheath 7 and against the proximal end of the plug 20. The push rod assembly maintains the plug in position within the ovarian pathway while the sheath 7 and wounding segment are pulled proximally within the catheter body 6 when the plug ejection mechanism is operated.

Figure 3:
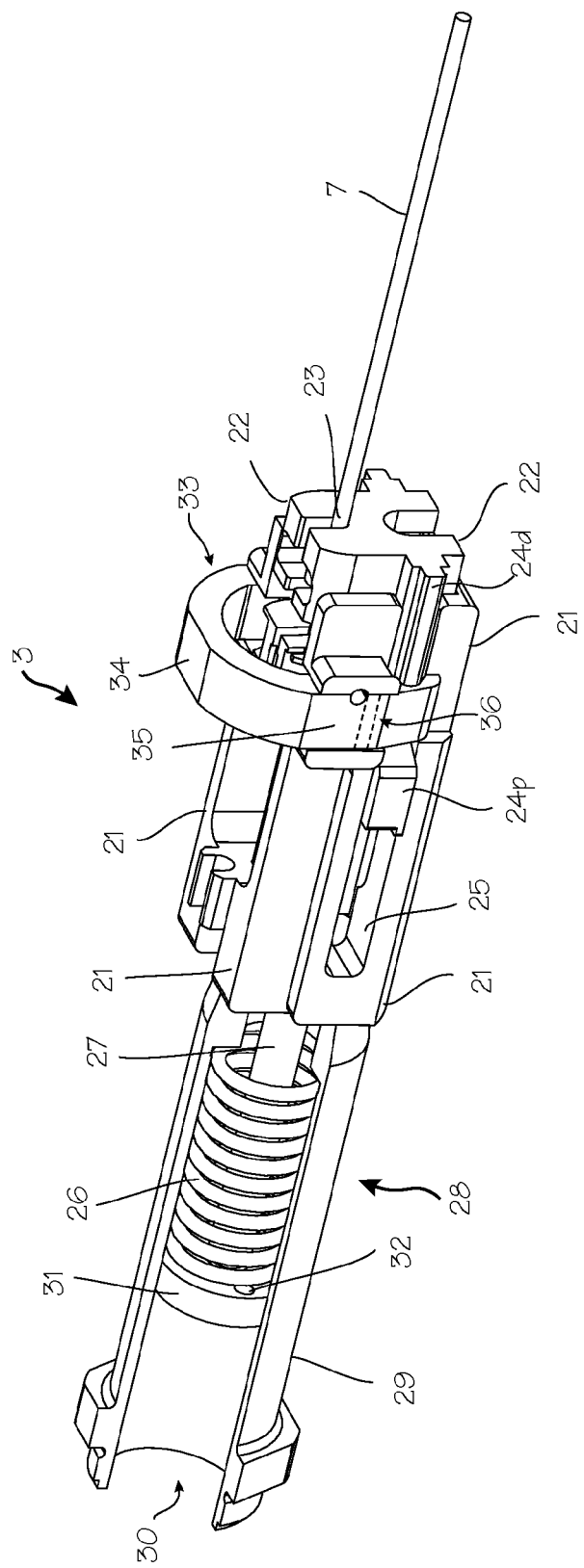
FIG. 3 shows a perspective view of the major components of the sheath retraction mechanism.

FIG. 3 shows a perspective view of the major components of the sheath retraction mechanism. The sheath retraction mechanism comprises a chassis 21 and a sliding hub 22 that is slidably engaged with the chassis. The chassis is fixedly attached to the housing of the handle shown in FIG. 1. The proximal end 23 of the sheath 7 is longitudinally fixed to the sliding hub. (The pushrod 18, hidden in this view, extends proximally beyond the proximal end of the catheter body, and is fixed to the chassis at the proximal end of the chassis.) Rail guides in the form of ridges or extensions 24d and 24p coupled to the sliding hub fit within rail slots 25 of the chassis, such that the sliding hub is slidably secured within the chassis. A spring 26 is operably coupled to the sheath through a piston rod 27 which is coupled and longitudinally fixed to the sliding hub. The spring is disposed within a dashpot 28 that comprises a cylinder 29 with a fluid-filled chamber 30. (The fluid within the chamber may be a liquid or gel having sufficient viscosity to regulate the expansion of the spring 26 and retract the sheath smoothly. Suitable fluids include materials such as silicone oil.) The spring engages a piston 31 slidably disposed within the chamber. The rod 27 is coupled to the piston at the rod's proximal end and coupled to the sliding hub at the rod's distal end. (Perforations 32 in the piston allow movement through the fluid within the chamber.) A latch 33 is used to hold the sliding hub in the distal position, and thus hold the spring in a compressed position, as shown in FIG. 3. The latch is U-shaped with a base 34 and extensions 35 that extend downward into interfering relationship with the distal rail guide 24d. The yoke is slidably disposed about the chassis and may slide up and down relative to the chassis and sliding hub. The extensions contain a channel 36 (shown in phantom) sized and dimensioned to accommodate the distal rail guides 24d. When the yoke is in an up position the yoke channel is misaligned with the rail guide, preventing proximal movement of the sliding hub. When the yoke is moved down such that the channel 36 is aligned with the rail guide, the system is unlatched and the sliding hub and sheath are pulled proximally by the expanding spring. (The components shown in this view are symmetrical about the long axis of the device, so that the hidden side of sheath retraction mechanism is identical to the illustrated view, but the device need not be symmetrical. Also, the dashpot assembly illustrated has the spring disposed within the fluid chamber of the dashpot, but the spring may be located in any other convenient position in the system (for example, proximal to the sliding hub).)

FIG. 4 illustrates the delivery catheter 1 with the plug ejection mechanism as it is configured prior to ejection of the plug. Here, the spring 26 is compressed within the cylinder 29. The sliding hub 22 is in a distal position within the handle 2. The yoke 33 is holding the sliding hub 22 in this position. A latch release button 37 is positioned above the yoke 33 in such a manner so as to impinge upon the yoke 33 when the push-button 37 is depressed. The channel 36 is misaligned with the rail guide 24 and the rail slot 25. The push rod assembly 18 is longitudinally fixed relative to the chassis 21 and handle. The sliding hub 22 is coupled to the sheath 7 at its proximal end by boss 38 (which is fixed to the proximal end of the sheath and captured within the sliding hub) but is not attached to the underlying push rod 18.

FIG. 5 shows the plug ejection mechanism after as it is configured after it has been activated and the plug 20 has been uncovered. In this view, the push-button 37 has been depressed and has moved the yoke 33 downward. When the button 37 is depressed and the yoke 33 is in a down position, the channel 36 is aligned with the rail guide 24 and the rail slot 25. Thus, the rail guide 24 is able to slide within the channel 24 along the slot 25 when the release button 37 is depressed. This allows the spring 26 to expand and force the piston, rod, sliding hub and sheath proximally relative to the chassis and handle, while the push rod 18 is held in place relative to the withdrawn sheath. Withdrawal of the sheath 7 within the catheter body 6 deposits the plug from the distal tip of the catheter without moving the plug relative to a wounded segment of the ovarian pathway after initial positioning (and also without moving the catheter body relative to the patient).

To provide feedback to the physician that the plug ejection is complete, a first contact 39 is disposed on a rail guide and a 30 second contact 40 is mounted on the wall of the handle or otherwise fixed relative to the handle and/or chassis. An electrical circuit is closed as long as the first and second contacts remain in electrical communication with one another. Energy can be supplied to the wounding element while this electrical communication is maintained. When the sheath retraction mechanism 3 is activated, the sliding hub 22 is forced proximally (and the sheath 7 is retracted), and the first contact slides past the second contact. The first and second contacts are no longer in electrical communication with one another when the sliding block is in the proximal position within the handle. The loss of contact is sensed by the control system, which provides visual or audio indication to the clinician indicating that the sheath has been withdrawn. The control system may also be programmed such that it will not provide power to the wounding segment if contact between the two electrodes has been broken. In conjunction with the control system, which is programmed to provide appropriate interface indications and apply power only if the contacts are in electrical communication, this limits the possibility that doctor might try to insert a catheter that is not properly loaded, or which has been used or prematurely released.

Figure 6:
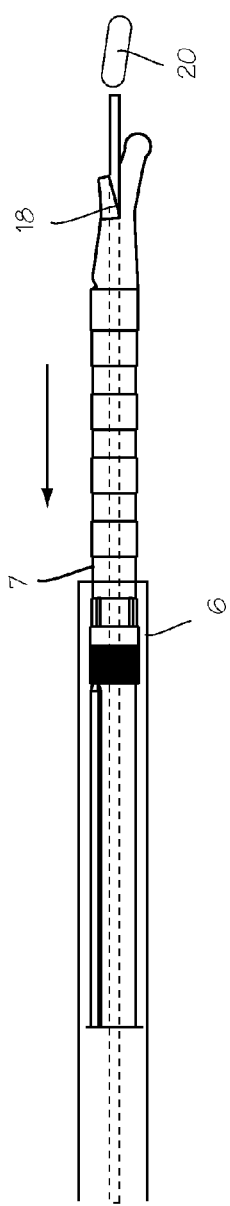
FIG. 6 shows the distal portion of the delivery catheter after the plug ejection mechanism has been activated and the plug has been uncovered.

FIG. 6 shows the distal portion of the delivery catheter after the plug ejection mechanism has been activated and the plug is ejected. As illustrated in FIG. 6, the plug 20 is uncovered and released by the retraction of the sheath 7 over the plug 20 as it is held in position by the push rod 18.

Figure 7:
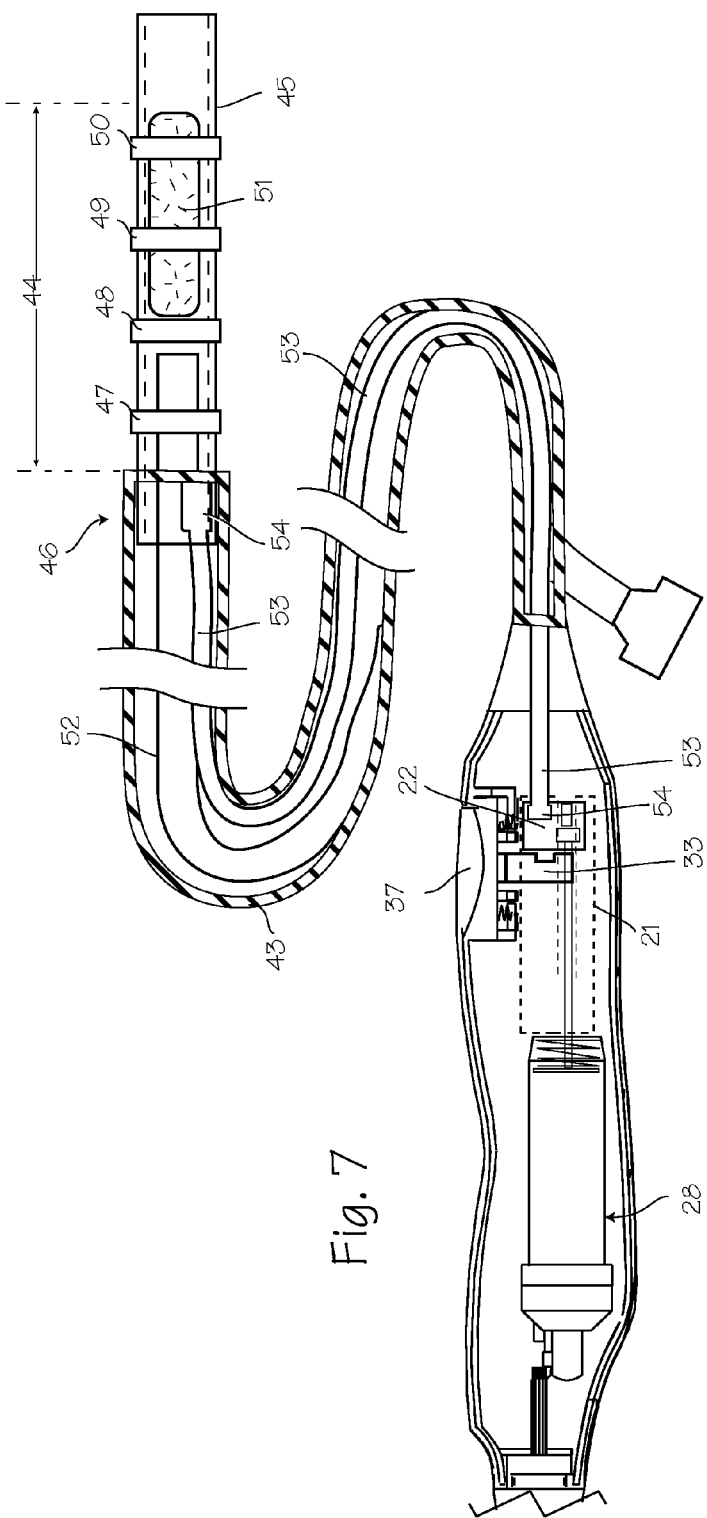
FIG. 7 illustrates a delivery catheter with the plug ejection mechanism adapted for use with the catheter construction depicted in our prior U.S. Pat. No. 6,309,384.

FIG. 7 illustrates a delivery catheter with the plug ejection mechanism adapted for use with the catheter construction depicted in our prior U.S. Pat. No. 6,309,384. As shown in FIG. 7, the delivery catheter comprises a catheter body 43 with a wounding segment 44 comprising a short tubular sheath 45 slidably mounted within the distal tip 46 of the catheter. The distal tip of the catheter body extends over the proximal end of the tubular extension for a short length. Four electrodes 47, 48, 49 and 50 are disposed along the outer surface of the wounding segment and wrap around the catheter. One or more foam plugs 51 are stored within the catheter body, and are shown housed within the wounding segment. A push rod 52 is disposed within the catheter body 43, fixed longitudinally within the catheter body at a point proximal to the wounding segment which permits adequate pullback of the wounding segment sheath 45 to uncover and release the plug, in contrast to the holding rod of FIGS. 1 through 5 which extends into the handle to a fixation point proximal to the proximal end of the catheter body. Unlike the sheath shown in FIGS. 1 through 5, the sheath 45 of FIG. 7 does not fully extend to the chassis 21 and is not directly coupled to the sliding hub 22. Instead, a pullwire 53 is secured to the proximal end of the sheath 45 and wounding segment by attachment of the boss 54 on the distal end of the pullwire 53. The pullwire 53 extends proximally from the wounding segment to the hub and is longitudinally fixed to the sliding hub 22. The dashpot 28, latch 33, and pushbutton 37 are arranged as described above. When the plug ejection mechanism is activated, the pullwire and the sheath 45 are retracted proximally as the sliding hub 22 slides proximally within the chassis 21. Thus, various arrangements of the translating components and fixed components of the system may be employed in the plug ejection mechanism.

In use, the clinician places the distal end of the catheter system at the appropriate location within the ovarian pathway of the patient, using appropriate visualization and manipulation the catheter with the handle. Thereafter, the clinician will operate the control system of the system to apply appropriate energy to the ovarian pathway proximate the wounding segment. Thereafter, the clinician, holding the catheter system in one hand or both hands, need only depress the push-button to release the plug into the wounded segment of the ovarian pathway. Using the configuration described above, all necessary manipulations may be accomplished one-handed, leaving the clinician's other hand free to manipulate the control system or a hysteroscope.

Figure 8:
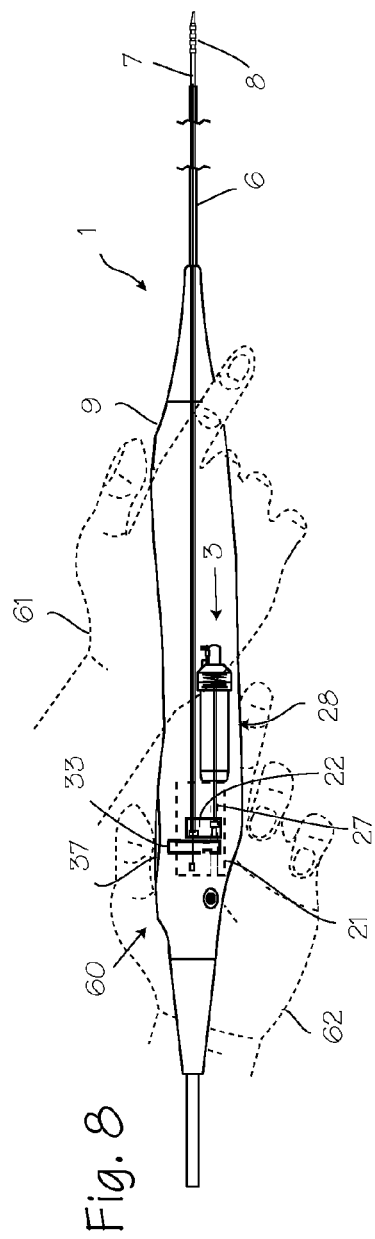
FIG. 8 shows a delivery catheter with the latch release button disposed in the proximal portion of the handle.

If it is desired to configure the device so as to inhibit one-handed operation, the device may be configured as shown FIG. 8, which illustrates a configuration of the handle and sheath retraction mechanism with the push-button disposed in the proximal portion of the handle, thereby encouraging two-handed use of the device. The delivery catheter of FIG. 8 includes the catheter shaft or body 6, a sheath 7 and housing 9. The plug ejection mechanism 3 is contained within the handle. A release button 37 operably coupled to the plug ejection mechanism is disposed in the proximal portion 60 of the handle. The shaft retraction mechanism is rearranged, with the dashpot 28 placed distally of the sliding hub 22, and the spring disposed to push, rather than pull, the sliding hub proximally. With this arrangement, with the housing held most conveniently, the push-button is disposed proximally of the clinician's preferred hand (the hand 61 used to manipulate the catheter), thus encouraging or requiring that the clinician use his other hand 62 to depress the push-button. This delivery catheter may require two hands to operate. The plug ejection mechanism may also be modified to use a spring that pulls on the piston rather than push against the piston in order to retract the sheath. The sheath may be pushed or pulled, so long as the sheath is retracted within the body.

Figure 9:
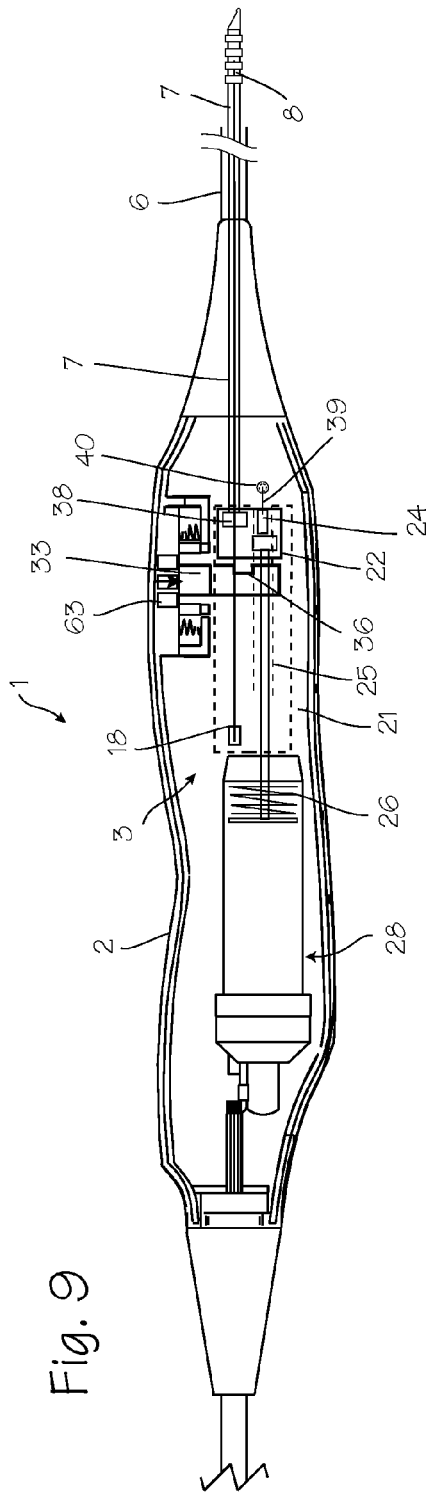
FIG. 9 shows a solenoid-operated version of the sheath retraction system of FIGS. 1 through 5.

The shaft retraction system can also be modified so that the clinician need not manually depress a push-button to force the latch downward. FIG. 9 shows a solenoid-operated version of the sheath retraction system of FIGS. 1 through 5. In FIG. 9, a solenoid 63 is operably coupled to the yoke and is used in place of a release button. Other components of the plug ejection mechanism, including the chassis 21, the sliding hub 22, the dashpot 28 and the latch 33 are arranged as shown in FIG. 4 or FIG. 8. In this device, the solenoid is placed in electrical communication with a control system. The control system is programmed to activate the plug ejection mechanism upon receipt of appropriate input from the operator, or immediately after the wounding energy has been applied. The solenoid operates to push the yoke downward to align the channels with the rail guide of the sliding hub and thereby permit proximal movement of the sliding hub. This "no-hands" configuration has the benefit that it can be controlled by the control system, and the control system can be further programmed to energize the solenoid (and eject the plug) only after the wounding segment has been operated, thereby avoiding inadvertent ejection or release without the requisite wounding steps.

The plug ejection mechanism and sheath retraction system can be adapted to deliver other contraceptive devices, occlusive devices intended for other lumens of the body, and other implants. Thus, while the preferred embodiments of the devices and methods have been described in reference to the environment in which they were developed, they are merely illustrative of the principles of the inventions. Other embodiments and configurations may be devised without departing from the spirit of the inventions and the scope of the appended claims.

We claim:

1. A device for fallopian tube occlusion detection, comprising:
   a handle;
   a catheter body longitudinally fixed relative to the handle, said catheter body having a distal end and a proximal end;
   a rod longitudinally fixed relative to the handle;
   a sheath slidably disposed about the rod, including a distal portion that is slidably extendable distally from the distal end of the catheter; and
   a sheath retraction mechanism disposed within the handle, said sheath retraction mechanism comprising
      a chassis fixedly coupled to the handle;
      a sliding hub slidably engaged with the chassis and fixed to the sheath;
      a fluid filled chamber;
      a piston disposed within the chamber;
      a piston rod coupled to the piston and the sliding hub; and
      a spring operably engaged with the piston;
      wherein the sheath retraction mechanism retracts the sheath when the spring is released, and said retraction is dampened by the fluid filled chamber.

2. The device of claim 1 further comprising:
   a latch configured to allow release of the spring and translation of the sheath;
   a pushbutton operable to impinge on the latch.

3. The device of claim 2 further comprising:
   a solenoid disposed proximate the latch, said solenoid being operable to impinge on the latch.

4. The device of claim 1, wherein:
   the proximal end of the catheter body is fixed to the handle;
   a proximal end of the sheath is fixed to the sliding hub; and
   the rod is longitudinally fixed to the handle at a point proximal of the proximal end of the sheath.

5. The device of claim 4, wherein:
   a proximal end of the rod extends proximally from the proximal end of the sheath, and is longitudinally fixed to the chassis at a point proximal of the proximal end of the sheath.

6. The device of claim 1 further wherein:
   the spring is disposed within the fluid-filled chamber, and is operably engaged with the piston.

* * * * *